(12) United States Patent
Campin et al.

(10) Patent No.: US 12,396,841 B2
(45) Date of Patent: Aug. 26, 2025

(54) METHODS AND SYSTEMS FOR DETERMINING INTRAOCULAR LENS (IOL) PARAMETERS FOR CATARACT SURGERY

(71) Applicant: Alcon Inc., Fribourg (CH)

(72) Inventors: John Alfred Campin, Southlake, TX (US); Horia Grecu, Berlin (DE); George Hunter Pettit, Fort Worth, TX (US); Mark Andrew Zielke, Lake Forest, CA (US); Peter Zieger, Berlin (DE)

(73) Assignee: ALCON INC., Fribourg (CH)

( * ) Notice: Subject to any disclaimer, the term of this patent is extended or adjusted under 35 U.S.C. 154(b) by 722 days.

(21) Appl. No.: 17/722,921

(22) Filed: Apr. 18, 2022

(65) Prior Publication Data

US 2022/0331092 A1 Oct. 20, 2022

Related U.S. Application Data

(60) Provisional application No. 63/176,600, filed on Apr. 19, 2021.

(51) Int. Cl.
*A61F 2/16* (2006.01)
*A61B 3/00* (2006.01)
*A61B 3/10* (2006.01)
*A61B 3/107* (2006.01)

(52) U.S. Cl.
CPC .............. *A61F 2/16* (2013.01); *A61B 3/0025* (2013.01); *A61B 3/1005* (2013.01); *A61B 3/102* (2013.01); *A61B 3/107* (2013.01)

(58) Field of Classification Search
CPC ....... A61F 2/16; A61B 3/0025; A61B 3/1005; A61B 3/102; A61B 3/107
USPC ............................................ 351/246
See application file for complete search history.

(56) References Cited

U.S. PATENT DOCUMENTS

| | | | |
|---|---|---|---|
| 2012/0287398 A1* | 11/2012 | Baker | A61B 3/103 351/201 |
| 2014/0125949 A1* | 5/2014 | Shea | A61B 3/1035 351/205 |
| 2015/0173600 A1* | 6/2015 | Campin | A61B 3/10 351/209 |
| 2019/0209242 A1* | 7/2019 | Padrick | G06N 20/00 |
| 2020/0229870 A1* | 7/2020 | Sarangapani | A61F 2/16 |

* cited by examiner

Primary Examiner — Mohammed A Hasan

(57) ABSTRACT

Certain aspects of the present disclosure provide techniques for performing surgical ophthalmic procedures, such as cataract surgeries. An example method generally includes generating, using one or more measurement devices, one or more data points associated with measurements of one or more anatomical parameters for an eye to be treated. Using one or more trained machine learning models, one or more recommendations are generated including one or more IOL parameters for the IOL to be used in the cataract surgery based, at least in part, on the one or more data points. The machine learning models are trained based on at least one historical data set of data points associated with measurements of anatomical parameters mapped to treatment data and treatment result data associated with each historical patient. The one or more IOL parameters comprise one or more of an IOL type, an IOL power, or IOL placement information for implanting the IOL in the eye.

25 Claims, 8 Drawing Sheets

METHODS AND SYSTEMS FOR DETERMINING INTRAOCULAR LENS (IOL) PARAMETERS FOR CATARACT SURGERY

INTRODUCTION

Aspects of the present disclosure relate to ophthalmic surgery, and more specifically to determining IOL parameters for performing cataract surgery on a patient using one or more machine learning models. As defined herein, IOL parameters include at least one of the type, power, and placement location of an IOL that is to be implanted in a patient's eye during cataract surgery.

BACKGROUND

Ophthalmic surgery generally encompasses various procedures performed on a human eye. These surgical procedures may include, among other procedures, cataract surgery, which is a procedure in which the natural lens of a human eye is replaced with a synthetic lens (also known as an intraocular lens (IOL)) to rectify vision problems arising from opacification of the natural lens. These IOLs come in various powers and types and may be selected based on measurements of anatomical parameters of a patient's eye. Further, the location of where an IOL is placed in the eye and the rotational orientation of the IOL (for certain types of IOLs, such as toric IOLs used to correct astigmatism), referred to herein as the "placement information," may also be based on the measurements anatomical parameters of the patient's eye.

Anatomical parameters of a human eye, such as the axial length (i.e., the distance between the anterior cornea and the retina), corneal thickness, anterior chamber depth (i.e., the distance between the anterior cornea and the anterior lens surface), white-to-white diameter (i.e., the distance between the corneal and scleral boundary on either side of the eye), lens thickness, and lens curvature, generally influence IOL parameter selections made in the planning and performing of cataract surgery on a patient. Planning and performing cataract surgery, as defined herein, includes determining the right IOL parameters for improving the patient's vision. As an example, based on the patient's measurements of anatomical parameters, a surgeon may try to determine the IOL type, power, and placement location that have a high likelihood of restoring the patient's vision. The surgeon then selects an IOL, from a plurality of IOLs, whose type and power match the determined IOL type and power. Subsequently, the surgeon places or implants the selected IOL in the lens capsule at the determined placement location.

The measurements of anatomical parameters for a specific patient, in many cases, may be within a known distribution (e.g., between a lower bound and an upper bound where some set percentage of patients are within, such as a normal distribution of two standard deviations from a global mean in which measurements for about 95 percent of patients lie) and, therefore, planning and performing cataract surgery for such a patient may be a more straightforward task.

However, if one or more anatomical parameters for a specific patient deviate from the known distribution or are otherwise abnormal (hereinafter "anomalous"), planning and performing cataract surgery for such a patient may be a more complicated task. Additionally, some cases may exist where each of the individual anatomical parameters are within a normal range, but the combination of anatomical parameters makes treatment of the eye a complicated task. For example, in such cases, the surgeon may select IOL parameters that may lead to an unsuccessful surgical outcome. Further, in some cases, regardless of whether the measurements of anatomical parameters for a patient's eye deviate from the known distribution, outcomes of a patient's cataract surgery may be optimized based on results of procedures performed on similar patients in the past.

Accordingly, techniques are needed for accurately determining IOL parameters for a patient based, at least in part, on measurements of anatomical parameters for the patient's eye.

BRIEF SUMMARY

Certain embodiments provide a method for determining one or more intraocular lens (IOL) parameters for an IOL to be used in a cataract surgery procedure. The method generally includes generating, using one or more measurement devices, data points associated with measurements of one or more anatomical parameters of an eye to be treated. Using one or more trained machine learning models, one or more recommendations are generated including one or more IOL parameters for the IOL to be used in the cataract surgery based, at least in part, on the generated data points associated with the measurements of the one or more anatomical parameters. The one or more trained machine learning models are trained based on at least one historical data set, wherein each entry in the historical dataset includes data points associated with measurements of anatomical parameters for a historical patient mapped to treatment data and treatment result data associated with the historical patient. The treatment data associated with the historical patient indicates at least one or more actual IOL parameters of a corresponding IOL used for treating the historical patient, and the treatment result data associated with the historical patient indicates at least one or more result parameters indicative of the historical patient's surgical outcome. The one or more IOL parameters comprise one or more of a type of IOL to use, a power of the IOL, or placement information for implanting the IOL in the eye.

Certain embodiments provide a method for performing a cataract surgery procedure. The method generally includes receiving data points associated with measurements of one or more anatomical parameters of an eye to be treated. Using one or more trained machine learning models, one or more recommendations are generated. The recommendations generally include one or more intraocular lens (IOL) parameters for the IOL to be used in the cataract surgery based, at least in part, on the data points associated with measurements of the one or more anatomical parameters. The one or more trained machine learning models are trained based on at least one historical data set, wherein each entry in the historical data set includes data points associated with measurements of anatomical parameters for a historical patient mapped to treatment data and treatment result data associated with the historical patient, the treatment data associated with the historical patient indicates at least one or more of actual IOL parameters of a corresponding IOL used for treating the historical patient, and the treatment result data associated with the historical patient indicates at least one or more result parameters indicative of the historical patient's surgical outcome. The one or more IOL parameters comprise one or more of a type of IOL to use, a power of the IOL, or placement information for implanting the IOL in the eye. The generated one or more recommendations for the cataract surgery are transmitted to a designated destination device.

Certain embodiments provide a method for training a machine learning model to generate recommendations for an ophthalmic treatment. The method generally includes generating a training data set from a set of historical patient records, wherein each record in the training data set corresponds to a historical patient and comprises information identifying: data points associated with measurements of one or more anatomical parameters for the historical patient, one or more intraocular lens (IOL) parameters of a corresponding IOL used for treating the historical patient, and one or more treatment result parameters indicative of the historical patient's surgical outcome. One or more machine learning models are trained based on the training data set to generate an output identifying at least one of a candidate intraocular lens (IOL) type, IOL power information, and IOL placement information for treatment of a current patient based at least on data points associated with measurements of one or more anatomical parameters for the current patient's eye. The trained one or more machine learning models are deployed to one or more computing systems.

Certain embodiments provide a method for performing a cataract surgery procedure. The method generally includes generating a training data set from a set of historical patient records, wherein each record in the training data set corresponds to a historical patient and comprises information identifying: data points associated with measurements of one or more anatomical parameters for the historical patient, one or more intraocular lens (IOL) parameters of a corresponding IOL used in a cataract surgery procedure performed on the historical patient, and treatment result data identifying an outcome of the intraocular treatment performed on the historical patient. One or more machine learning models are trained based on the training data set to generate an output identifying at least one of a candidate IOL type, IOL power information, and IOL placement information for treatment of a current patient based at least on one or more data points associated with measurements of anatomical parameters for the current patient's eye. Data points associated with measurements of one or more anatomical parameters of the current patient's eye are generated using one or more measurement devices. Based on a comparison of the one or more data points to a distribution of measurements representing nonanomalous data points for historical patients, it is determined that at least one of the data points corresponds to an anomalous measurement. Based on determining that at least one of the one or more data points corresponds to an anomalous measurement, one or more recommended IOL parameters for the current patient's eye are generated, using the one or more trained machine learning models based, at least in part, on the one or more data points, wherein the one or more recommended IOL parameters comprise one or more of an IOL type, an IOL power, or an IOL placement location for implanting the IOL in the eye.

Aspects of the present disclosure provide means for, apparatus, processors, and computer-readable mediums for performing the methods described herein.

To the accomplishment of the foregoing and related ends, the one or more aspects comprise the features hereinafter fully described and particularly pointed out in the claims. The following description and the appended drawings set forth in detail certain illustrative features of the one or more aspects. These features are indicative, however, of but a few of the various ways in which the principles of various aspects may be employed.

BRIEF DESCRIPTION OF THE DRAWINGS

The appended figures depict certain aspects of the one or more embodiments and are therefore not to be considered limiting of the scope of this disclosure.

To facilitate understanding, identical reference numerals have been used, where possible, to designate identical elements that are common to the drawings. It is contemplated that elements and features of one embodiment may be beneficially incorporated in other embodiments without further recitation.

DETAILED DESCRIPTION

Figure 1A:
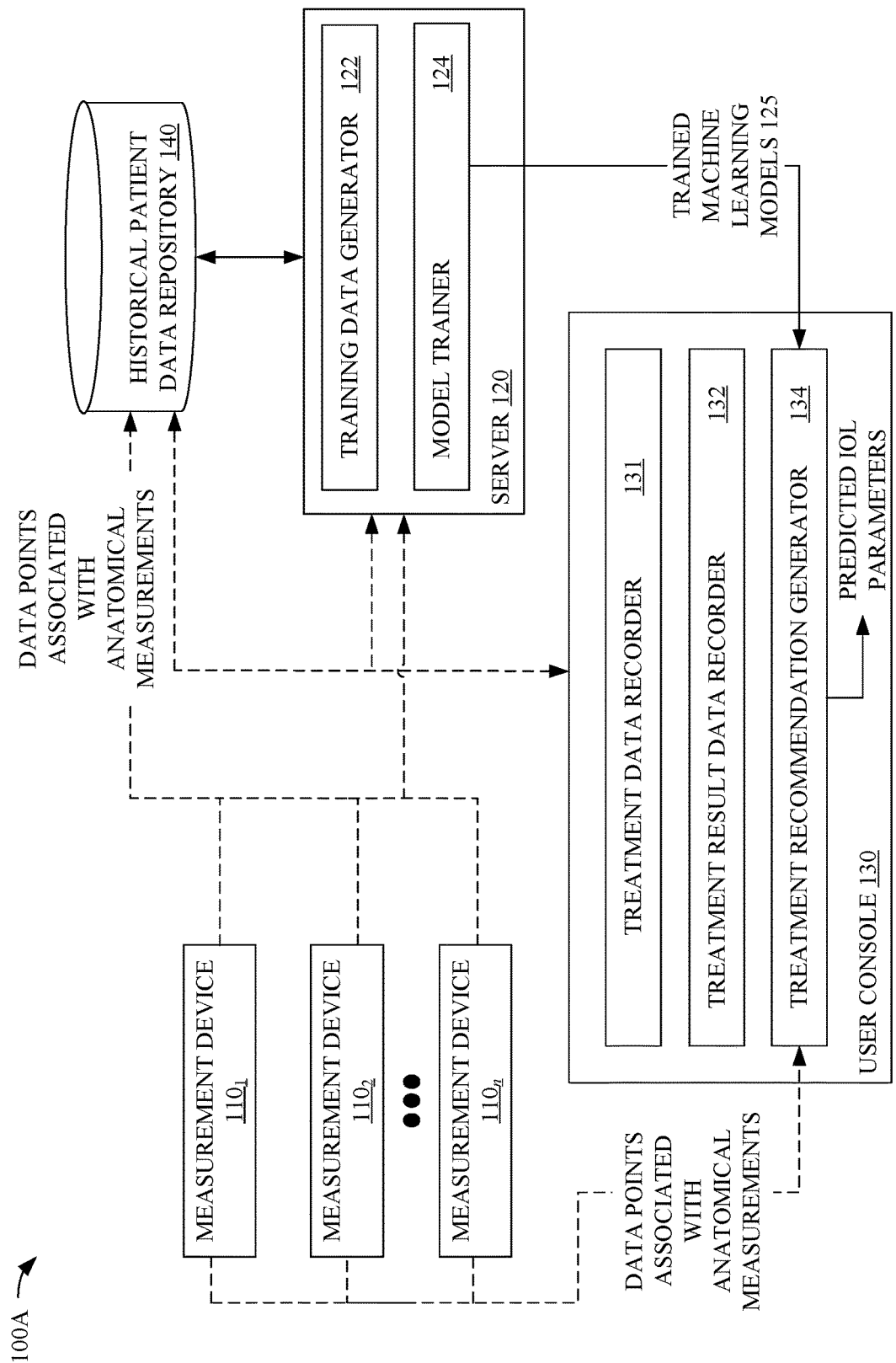
FIGS. 1A-1C depicts an example environment in which one or more machine learning models are trained and deployed for use in generating recommendations, including IOL parameters, for a patient's cataract surgery based at least on the patient's data points associated with measurements of anatomical parameters, in accordance with certain aspects described herein.

As discussed above, cataract surgery is a surgical procedure in which a defective natural lens is replaced with an IOL. Typically, a defective natural lens is a lens that has developed a cataract, which is an opacification of the natural lens that negatively affects the patient's vision (e.g., causing a patient to see faded colors, have blurry vision or double vision, see haloing around point light sources, or other negative effects). An IOL may be selected to replace the patient's natural lens in order to restore, or at least improve, the patient's vision. The determination of a set of IOL parameters, for an IOL to be used for a patient, may be influenced by a number of the patient's data points associated with measurements of anatomical parameters. More specifically, as discussed, based on the characteristics and/or measurements of a patient's eye, a surgeon may try to determine a set of IOL parameters that have a high likelihood of restoring the patient's vision. For example, some IOLs may allow for optimized near or far vision, while other IOLs may be used to compensate for a patient's natural corneal astigmatism, and so on. Generally, where the anatomical measurements for a patient are within a range of typical values for these anatomical measurements or where the anatomical measurements in the aggregate are within the range of typical values, determining the IOL parameters for the patient may be a routine task for which a surgeon can use prior experience with many other past patients. However, where one or more of the anatomical measurements deviate from the range of typical values or where the anatomical measurements in the aggregate deviate from the range of typical values, a surgeon may not be able to draw on prior experience in order to determine an optimal treatment for the patient, including determining the IOL parameters.

Aspects presented herein provide systems in which machine learning models are trained based on historical patient data to determine IOL parameters for a current patient. As defined herein, a new or current patient (hereinafter "current") is generally a patient who is having cataract surgery to replace a defective natural lens, and as discussed in further detail below, the recommended IOL parameters for the current patient may be generated by machine learning models that are trained to generate these parameters based on IOL parameters associated with similar past patients and the outcomes reported by those other patients. By using these machine learning models, a large universe of historical patient data can be leveraged to generate recommended and contraindicated IOL parameters for the current patient. This large universe of historical patient data is, in a way, indicative of the expertise and prior experiences of other surgeons who have handled similar surgeries for similar patients. By using the systems and methods described herein, for a current patient, the surgeon is able to leverage this large universe of historical patient data in order to determine IOL parameters that would result in optimized surgical outcomes for the current patient. Accordingly, the techniques herein improve the medical field by allowing for better IOL parameters to be selected, thereby leading to improved vision after placement of an IOL, such as during cataract surgery.

Figure 1B:
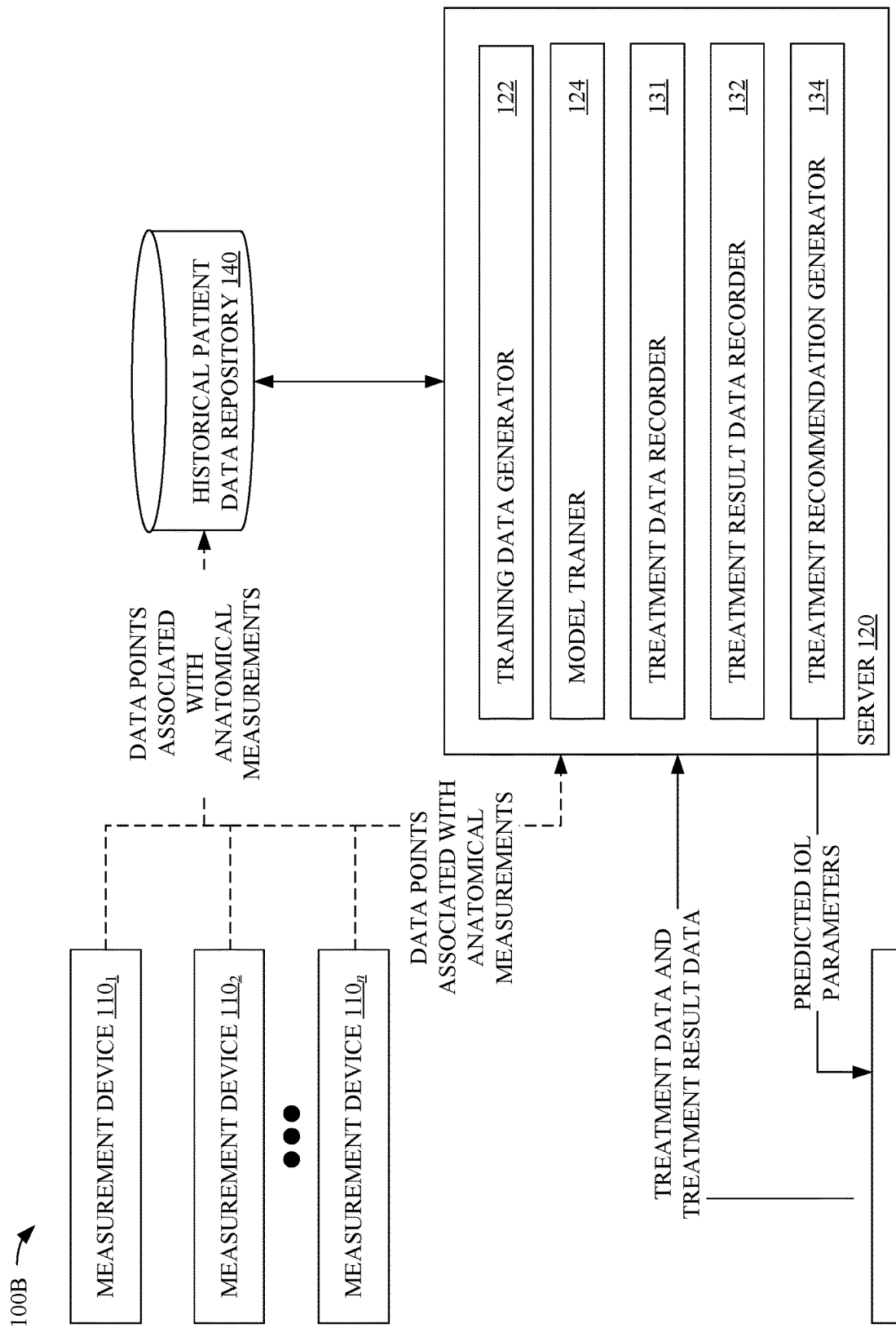
Figure 1C:
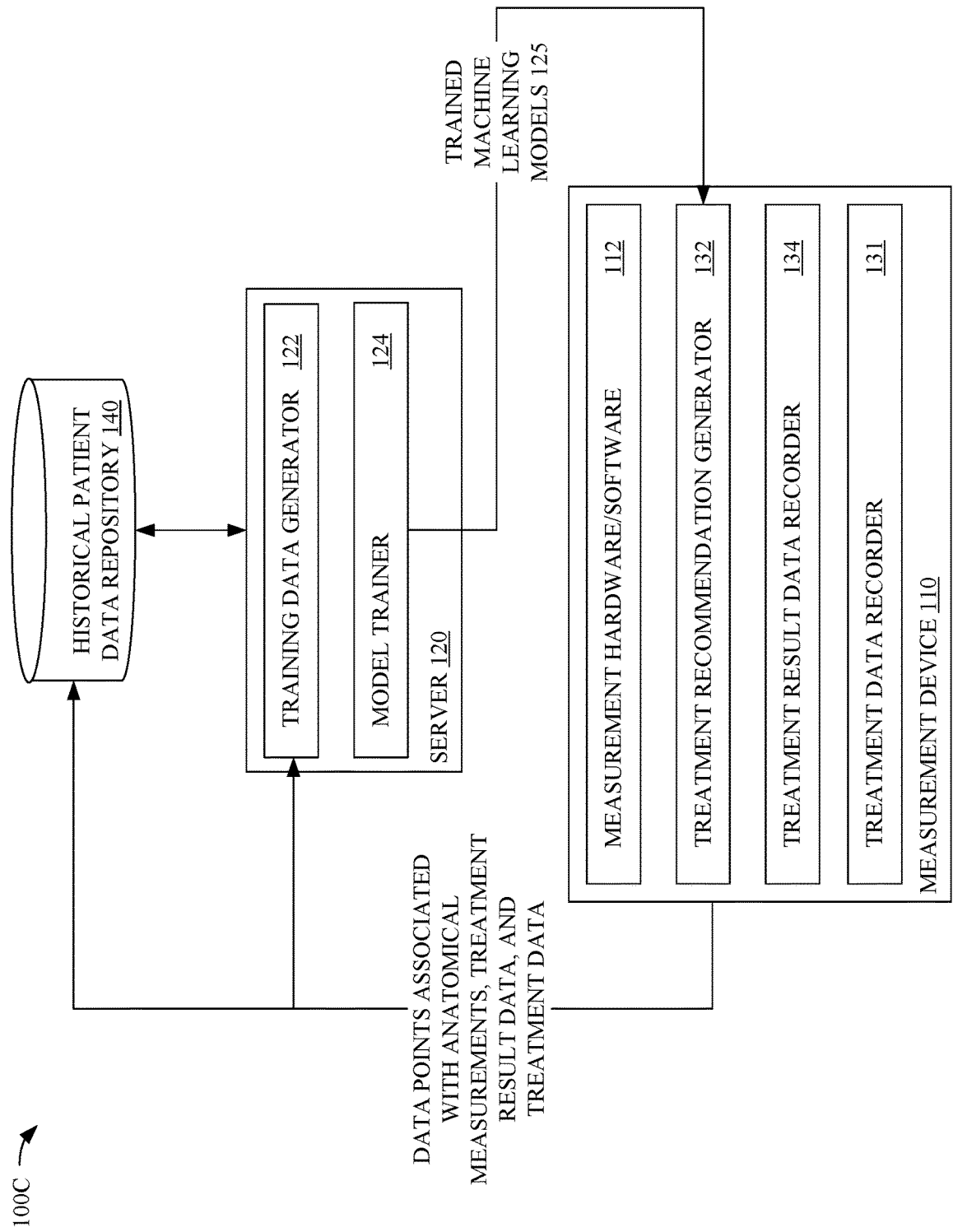

Example Computing Environment for Optimizing Ophthalmic Surgery Procedure Planning FIGS. 1A-1C illustrate example computing environments in which machine learning models are trained and used in generating recommendations, including IOL parameters, for a patient's cataract surgery. Generally, these machine learning models may be trained using a corpus of training data including records corresponding to historical patient data and deployed for use in generating IOL parameters to be used for performing cataract surgery on a current patient. Historical patient data for each historical patient may include the patient's demographic information, recorded data points associated with measurements of anatomical parameters, desired outcomes, actual treatment data such as actual IOL parameters (e.g., IOL type, power, and placement information), as well as other information about the historical patient's treatment, and the treatment result data (e.g., result parameters indicating the historical patient's satisfaction or dissatisfaction with the treatment). Note that, herein, actual treatment data indicates information about the actual treatment performed on the patient, as opposed to a recommended treatment. For example, actual treatment data may indicate actual IOL parameters, such as actual IOL type, power, and placement information, of an IOL that was implanted in the historical patient's lens capsule.

These machine learning models may be configured, as discussed in further detail below, to use at least the data points associated with measurements of anatomical parameters for a current patient, as input, and generate, as output, one or more recommendations, including one or more IOL parameters for the current patient. For example, these IOL parameters may include optimal IOL parameters as well as contraindicated or otherwise undesirable IOL parameters. Herein, optimal IOL parameters refer to IOL parameters that may have a high (e.g., the highest) likelihood of restoring or improving the patient's vision. On the other hand, contraindicated IOL parameters refer to IOL parameters that would likely result in a negative surgical outcome for the current patient.

As a result, the surgeon can be made aware of both optimal IOL parameters that, for similar patients, have historically resulted in positive surgical outcomes as well as contraindicated IOL parameters that, for similar patients, have historically resulted in negative surgical outcomes. Using this information, the surgeon is able to increase the likelihood of a positive surgical outcome for the current patient. Note that, as described in further detail below, the input to these machines learning models may include additional information, such as the current patient's demographic information, desired outcomes, additional patient and treatment relation information, etc. Also, in addition to the IOL parameters, recommendations that are provided by these machine learning models may further include certain surgical techniques, tools, additional treatment recommendation, etc.

Various techniques may be used to train and deploy machine learning models that generate IOL parameters for a current patient. Various deployments are illustrated in FIGS. 1A-1C. For example, FIG. 1A illustrates a deployment in which machine learning models are trained on a remote server and deployed to a user console used by a surgeon during cataract surgery. FIG. 1B illustrates a deployment in which the machine learning models are trained and deployed on a remote server accessible through the user console. Finally, FIG. 1C illustrates a deployment in which the machine learning models are trained on a remote server and deployed to a computing system integral with a measurement device used by a surgeon. It should be recognized, however, that various other techniques for training and deploying machine learning models that generate IOL parameters for a current patient may be contemplated, and that the deployments illustrated in FIGS. 1A-1C are non-limiting, illustrative examples.

FIG. 1A illustrates an example computing environment 100A in which measurement devices 110, server 120, and user console 130 are connected via a network in order to train one or more machine learning models for use in generating IOL parameters for a current patient based, at least in part, on the data points associated with measurements of anatomical parameters for the current patient, as provided by the measurement devices 110. For readability, the one or more machine learning models are referred to herein as "ML models," and cover both a single ML model and multiple ML models.

Measurement devices 110 are generally representative of various devices that can generate data points associated with one or more measurements of anatomical parameters of a patient's eye. Herein, anatomical parameters of an eye refer to parameters such as the axial length (e.g., the distance from the anterior cornea to the retina), a central corneal thickness measurement, an anterior chamber depth (e.g., the distance from the anterior cornea to the anterior lens surface), white-to-white diameter (e.g., the distance between the corneal or scleral boundary on each side of the eye), a lens thickness, curvature and astigmatism of the front corneal surface of the eye, the anterior corneal shape, etc. The data points may, in some embodiments, include measurements, i.e., measurement values, of the corresponding anatomical parameters. In some embodiments, the data points may include raw data from which measurements may be derived. In such a case, the raw data may include, for example, two-dimensional cross-sectional images showing the cornea, iris, lens, and retina; three-dimensional images of the eye; two-dimensional topographic maps of the eye; or other data from which measurements of anatomical parameters may be derived. Generally, any number of measurement devices $110_1$-$110_n$ may be included in computing environment 100A and may be used to generate different types of data that may be used as input into one or more machine learning models that generate IOL recommendations. Each measurement device 110 in the computing environment 100A may generate data points associated with measurements of one or more anatomical parameters of a patient's eye and provide the data points to user console 130, server 120, and/or repository 140.

In one example, one of measurement devices 110 may be an optical coherence tomography (OCT) device that can generate a two-dimensional cross-sectional image of the current patient's eye from which measurements of various anatomical parameters may be derived. The two-dimensional cross-sectional image may show the location of the cornea, lens, and retina on a two-dimensional plane (e.g., with the cornea on one side of the two-dimensional cross-section and the back of the retina on the other side of the two-dimensional cross-section). From the two-dimensional cross sectional image of the current patient's eye, the OCT device can derive various measurements. For example, the OCT device can generate, from the cross-sectional image, an axial length measurement, a central corneal thickness measurement, an anterior chamber depth measurement, a lens thickness measurement, and other relevant measurements. In some aspects, an OCT device may generate one-dimensional data measurements (e.g., from a central point) or may generate three-dimensional measurements from which additional information, such as tissue thickness maps, may be generated.

Another one of measurement devices 110 may be a keratometer. Generally, a keratometer may reflect a light pattern, such as a ring of illuminated dots, off of the current patient's eye and capture the reflected light pattern. The keratometer can perform an image analysis on the reflected pattern (relative to pattern output by the measurement device 110 for reflection from the current patient's eye) to measure or otherwise determine values for various anatomical parameters. These anatomical parameters may include, for example, curvature information and astigmatism information for the front corneal surface of the current patient's eye. The curvature information may, for example, be a general curvature measurement, a maximum curvature and axial information identifying the axis along which the maximum curvature occurs, and a minimum curvature and axial information identifying the axis along which the minimum curvature occurs.

Yet another one of the measurement devices 110 may be a topography device that measures the topography of the anterior corneal shape. The topography device may use a reflected light pattern analysis distributed over the corneal region to generate a detailed surface profile map relative to a base profile. For example, as the cornea is typically spherical or nearly spherical, the surface profile map can show deviations from the base profile, where different colors represent an amount of deviation from the base profile at any discrete point along the cornea.

Server 120 is generally representative of a single computing device or cluster of computing devices on which training datasets can be generated and used to train one or more machine learning models for generating IOL parameters. Server 120 is communicatively coupled to historical patient data repository 140 (hereinafter "repository 140"), which stores records of historical patients. In certain embodiments, repository 140 may be or include a database server for receiving information from server 120, user console 130, and/or measurement devices 110 and storing the information in corresponding patient records in a structured and organized manner.

In certain aspects, each patient record in repository 140 includes information such as the patient's demographic information, data points associated with measurements of anatomical parameters, actual treatment data associated with the patient's cataract surgery, and treatment results data. For example, the demographic information for each patient includes patient age, gender, ethnicity, and the like. The data points associated with measurements of anatomical parameters may include raw data generated by or measurements derived from or provided by an OCT device, a keratometer, a topography device, etc., as discussed above. As further elaborated below, the actual treatment includes the actual IOL parameters (IOL type, IOL power, IOL placement information) of an IOL used for the patient, as well as any additional relevant information relating to the treatment of the patient. For example, the treatment data may indicate the method of performing the cataract surgery for the patient, the tools that were used for the treatment, and other information about the specific procedures performed during the surgery. Each patient record also includes treatment result data, which may include various data points indicative of result parameters, such as the patient's satisfaction with the treatment such as a binary indication of satisfaction or dissatisfaction with the results of the surgery, measured vision levels after treatment, or the like.

Server 120 uses these records of historical patients to generate datasets for use in training ML models that can recommend IOL parameters to a surgeon for treating a current patient. More specifically, as illustrated in FIG. 1A, server 120 includes a training data generator 122 (hereinafter "TDG 122") and model trainer 124. TDG 122 retrieves data from repository 140 to generate datasets for use by model trainer 124 to train ML models 125.

Model trainer 124 includes or refers to one or more machine learning algorithms (referred to hereinafter as "ML algorithms") that are configured to use training datasets to train ML models 125. In certain embodiments, a trained ML model refers to a function, e.g., with weights and parameters, that is used to generate or predict one or more IOL parameters for a given set of inputs. Various ML algorithms may be used to generate different types of outputs for a given set of inputs.

The ML algorithms may generally include a supervised learning algorithm, an unsupervised learning algorithm, and/or a semi-supervised learning algorithm. Unsupervised learning is a type of machine learning algorithm used to draw inferences from datasets consisting of input data without labeled responses. Supervised learning is the machine learning task of learning a function that, for example, maps an input to an output based on example input-output pairs. Supervised learning algorithms, generally, include regression algorithms, classification algorithms, decision trees, neural networks, etc. A description of a labeled dataset is provided below.

Once trained and deployed, based on a certain set of inputs, including the data points associated with measurements of anatomical parameters for a current patient, the ML models 125 are able to generate or predict optimal IOL parameters for a current patient, as output. In certain aspects, model trainer 124 trains a single multi-input-multi-output (MIMO) ML model 125 that is configured to take a set of inputs associated with a current patient and provide all the IOL parameters to the surgeon who is performing cataract surgery on the current patient. For example, model trainer 124 may train a single model that takes a set of inputs associated with the current patient and outputs multiple IOL parameters, including the IOL type, IOL power, IOL placement information. To train a MIMO ML model 125, model trainer 124 may utilize a labeled dataset provided by TDG 122 that includes a plurality of samples indicating demographic information, data points associated with measurements of anatomical parameters, treatment data, and treatment results data for historical patients who reported positive surgical outcomes.

For example, each sample in such a labeled dataset includes one or more of i) input data including one or more of a historical patient's age, gender, ethnicity, race, data points associated with measurements of anatomical parameters for the patient generated by a number of measurement devices (e.g., an OCT device, a keratometer, and/or a topography device), surgical tools and procedures used to treat the patient, or the like; ii) output data including the actual IOL parameters (i.e., Y) used for treating the patient (e.g., IOL type, IOL power, and IOL placement information for the patient), and iii) treatment result information (e.g., patient-reported outcomes of the treatment). To train the MIMO ML model 125, model trainer 124 runs input data of each sample through the multi-input-multi-output ML model 125 to generate a set of optimal IOL parameters (i.e., Y^) that would hypothetically result in achieving a positive surgical outcome.

Model trainer 124 then trains the MIMO ML model 125 based on the resulting error (i.e., Y-Y^), which refers to the difference between the IOL parameters predicted by the MIMO ML model 125 and the actual IOL parameters used for the patient, as indicated in the patient record. In other words, model trainer 124 adjusts the weights in the ML model 125 to minimize the error (or divergence) between the predicted IOL parameters and the actual treatment used for the patient. For example, the model trainer 124 adjusts the weights to minimize the error between the predicted IOL parameters and the actual IOL parameters used for treatment of the patient that were indicated as having a positive surgical outcome. By running many more samples, i.e., additional historical patient information, through the MIMO ML model 125 and continuing to adjust the weights, after a certain point, MIMO ML model 125 starts making very accurate predictions with a very low error rate. At that point, MIMO ML model 125 is ready to be deployed for taking a set of inputs about a current patient and predicting optimal IOL parameters that would result in a positive surgical outcome for the current patient. In the example of FIG. 1A, the trained MIMO model 125 may then be deployed for use at user console 130 for predicting IOL parameters for a current patient, as described in further detail below.

In certain aspects, instead of training a MIMO ML model, model trainer 124 trains multiple multi-input-single-output (MISO) ML models 125 for separately predicting each of the IOL parameters for a current patient. In such aspects, each of the MISO ML models 125 takes a set of inputs associated with the current patient and outputs a single IOL parameter.

For example, a first ML model is trained to generate or predict the IOL type for the current patient as output, a second ML model is trained to generate or predict the IOL power for the current patient as output, and a third ML model is trained to generate or predict the IOL placement information for the current patient as output.

To train each of the MISO ML models 125, model trainer 124 may use datasets provided by TDG 122, each including demographic information, data points associated with measurements of anatomical parameters, actual treatment data, and treatment result data for historical patients who reported positive surgical outcome. For example, to train a MISO ML model 125 that is configured to predict the IOL type for a current patient, model trainer 124 uses a dataset including demographic information, data points associated with measurements of anatomical parameters, the actual IOL type, and treatment result data for historical patients who reported a positive surgical outcome. To ensure the MISO ML model 125, in such an example, makes accurate predictions, as discussed, model trainer 124 runs many samples in the corresponding dataset through the MISO model 125 until the prediction error (i.e., Y-Y^) is minimized. Model trainer 124 may similarly train additional MISO models for predicting the IOL power and IOL placement location.

Generally, the output of the MISO models includes a recommended IOL type, IOL power, and IOL placement information over a universe of possible IOL types, powers, and placements. For example, the MISO models may individually output a single recommendation from the universe of possible IOL types, IOL powers, and IOL placements, and these single recommendations may correspond to an IOL type, IOL power, and IOL placement that is most likely to result in a positive surgical outcome for the current patient. In another example, the MISO models may output a probability distribution over a universe of possible IOL types, powers, and placements. For example, the recommended IOL type may correspond to the IOL type having the highest probability score in the probability distribution for IOL types; the recommended IOL power may correspond to the IOL power having the highest probability score in the probability distribution for IOL powers; and the recommended IOL placement may correspond to the IOL placement having the highest probability score in the probability distribution for IOL powers. In the example of FIG. 1A, the trained MISO models 125 may then be deployed for use at user console 130 for predicting IOL parameters for a current patient, as described in further detail below.

In some aspects, ML models 125 may be deep learning models that are trained to generate recommended IOL parameters. These deep learning models may include, for example, convolutional neural networks (CNNs), adversarial learning algorithms, generative networks, or other deep learning algorithms that can learn relationships in data sets that may not be explicitly defined in the data used to train such models. In such a case, ML models 125 may be trained using raw data captured by measurement devices 110, such as two-dimensional or three-dimensional images from which typical numerical measurements of anatomical parameters can be derived. ML models 125 may, for example, map an input to different neurons in one or more layers of a deep learning model (e.g., where the ML models are generated using neural networks), where each neuron in the ML models 125 represents new features in an internal representation of an input that are learned over time. These neurons may then be mapped to an output representing recommended IOL parameters, as discussed above.

After ML models 125 are trained, model trainer 124 deploys the ML models 125 to user console 130 for use in predicting IOL parameters for a current patient. The measurement devices 110 generate data points associated with measurements of the anatomical parameters of the current patient's eye and transmit these data points to server 120, user console 130, and/or repository 140. Note that in embodiments where measurements device 110 transmit the data points to server 120 or user console 130 (as opposed to directly transmitting them to repository 140), the data points may at some later point be committed by server 120 or user console 130 to repository 140, which stores the measurements in the current patient's record.

Prior to surgery, user console 130 retrieves the data points (from the repository 140 or from temporary memory at the user console 130) and inputs the data points and other patient information (e.g., the current patient's demographic information, etc.) into the ML models 125. User console 130 then outputs the recommendations generated by the ML models 125. After surgery is completed for the current patient, user console 130 provides the actual treatment data (which may be the same or different from the recommended treatment) to the server 120 and/or repository 140. Note that actual treatment and the recommended treatment may be different because the surgeon may choose not to follow the recommended treatment (e.g., recommended IOL parameters). The current patient's actual treatment data is then stored in the current patient's record at repository 140.

Information about whether the current patient was satisfied with the outcome of the cataract surgery is later used to augment the current patient's record in the repository 140. More specifically, the current patient's satisfaction information is stored in the patient's record as treatment result information. This satisfaction information is received and stored by repository 140 from user console 130, server 120, or other computing devices (not shown).

The record in the repository 140, including the data points associated with the current patient's measurements for one or more anatomical parameters, the actual treatment data, and the treatment result data, is then converted into a new sample in a training data set that is used to retrain the ML models 125. More generally, each time a new (i.e., current) patient is treated, information about the new patient may be saved in repository 140 to supplement the training data set(s), and the supplemented training data set(s) may be used to retrain the ML models 125.

As discussed, the datasets used for training ML models 125 are generated by TDG 122. For example, TDG 122 may access all the patient records in repository 140 and generate datasets for use by model trainer 124. As discussed above, in certain aspects, TDG 122 may generate training data sets based on whether model trainer 124 is configured to train a MIMO ML model or a number of MISO ML models. For example, where model trainer 124 is configured to train a MIMO ML model, TDG 122 may be configured to generate a single training data set including patient's demographic information, data points associated with measurements of anatomical parameters, actual treatment data (actual IOL type, IOL power, and IOL placement location), and treatment result data for the patients. On the other hand, in aspects where model trainer 124 is configured to train multiple MISO ML models, TDG 122 may be configured to generate multiple training data sets. For example, a first training data set may be used to train a MISO model 125 for predicting an IOL type for a current patient given the data points associated with measurements of anatomical parameters for the current patient, a second training data set may be used to train a MISO ML model 125 for predicting an IOL power for the current patient given the data points associated with measurements of anatomical parameters for the current patient, and a third training data set may be used to train a MISO ML model 125 for predicting IOL placement information for the current patient given the data points associated with measurements of anatomical parameters for the current patient.

In some aspects, TDG 122 may generate datasets used by model trainer 124 to train contraindicated ML models that identify contraindicated IOL parameters for a current patient. In certain aspects, training datasets used for training such contraindicated ML models may be generated based on whether model trainer 124 is configured to generate multiple MISO contraindicated models or a single contraindicated MIMO model. For example, where model trainer 124 is configured to train a MIMO contraindicated ML model, TDG 122 may be configured to generate a training dataset that includes data points associated with measurements of anatomical parameters, treatment data, and treatment result information for patients who ultimately reported negative surgical outcomes. Similarly, where model trainer 124 is configured to train multiple MISO contraindicated models, TDG 122 may be configured to generate multiple training datasets. A first training dataset may correlate data points associated with measurements of anatomical parameters to an IOL type for patients that reported negative surgical outcomes, a second training data set may correlate data points associated with measurements of anatomical parameters to an IOL power for patients that reported negative surgical outcomes, and a third training data set may correlate data points associated with measurements of anatomical parameters to an IOL placement location for patients who reported negative surgical outcomes.

Once the trained ML models 125 are deployed, as further described below, TDG 122 continues to augment the training datasets with information relating to patients for whom the deployed ML models 125 provided predicted IOL parameters. For example, in the embodiments of FIG. 1A, a surgeon may use user console 130 to predict, using the deployed ML models 125, optimal IOL parameters for a new patient. In that example, as described above, a new record is then added to repository 140 that may include information about the new patient, including demographic information, data points associated with measurements of anatomical parameters, actual treatment data (e.g., the IOL parameters used for the patient), and/or treatment results information. TDG 122 then augments the dataset(s) for retraining the ML models 125. In certain aspects, TDG 122 augments the dataset(s) every time information about a new (i.e., current) patient becomes available. In certain other aspects, TDG 122 augments the dataset(s) with a batch of new patient records, which may be more resource efficient. For example, once the number of new patient records hit 100 (or, more generally, some threshold number), TDG 122 may augment the dataset(s) using information associated with the 100 new patient records. In such an example, a 100 new samples are then made available to model trainer 124 to retrain ML models 125 with.

User console 130 is generally representative of a computing device or system that is communicatively coupled to server 120, repository 140, and/or measurement devices 110. In certain embodiments, user console 130 may be a desktop computer, laptop computer, tablet computer, smartphone, or other computing device(s). For example, user console 130 may be a computing system used at the surgeon's office or clinic. In another example, user console 130 may be a surgical console used by a surgeon in an operating room to perform cataract surgery for a current patient. In such an example, the surgical console may drive one or more tools, including a phacoemulsification probe for emulsifying and aspirating the patient's lens.

In the example of FIG. 1A, the trained ML models 125 are deployed by server 120 to user console 130 for predicting, for a current patient, IOL parameters that would optimize the patient's surgical outcomes. As illustrated, user console 130 includes a treatment data recorder ("TDR") 131, a treatment result data recorder ("TRDR") 132, and a treatment recommendation generator ("TRG") 134.

TRG 134 generally refers to a software module or a set of software instructions or algorithms, including ML models 125, which take a set of inputs about a current patient and generate, as output, IOL parameters. In certain embodiments, TRG 134 is configured to receive the set of inputs from at least one of repository 140, measurement devices 110, a user interface of user console 130, and other computing devices that a medical team may use to record information about the current patient. In certain embodiments, TGR 134 outputs the IOL parameters to a display device communicatively coupled with user console 130, prints the recommended IOL parameters, generates and transmits one or more electronic messages, including the IOL parameters, to a destination device (e.g., a connected device, such as a tablet, smartphone, wearable device, etc.), or the like.

In some aspects, based on the data points associated with measurements of anatomical parameters for a current patient, TRG 134 may initially determine whether one or more of the data points corresponds to an anomalous measurement. Generally, an anomalous measurement may be a measurement that deviates from a typical distribution of normal measurements for a particular anatomical parameter or are measurements that are otherwise unclear or ambiguous. In certain aspects, to determine whether one or more of the current patient's anatomical measurements corresponds to an anomalous measurement, TRG 134 may use a trained and deployed ML model 125 that is configured to classify data points associated with measurements of anatomical parameters as anomalous or non-anomalous. In one example, such an ML model 125 may have been trained with a supervised learning classification algorithm, using a dataset that labels the data points associated with measurements of anatomical parameters of historical patients as either anomalous or non-anomalous.

If the data points for the current patient are within the known typical distribution of measurements, TRG 134 can indicate to a user of the user console 130 that the data points associated with measurements of anatomical parameters for the current patient are not anomalous. In such a case, TRG 134 may defer generating IOL parameters until a user explicitly requests user console 130 for the predicted IOL parameters through user input. If, however, at least one of the data points is determined to be anomalous, TRG 134 can indicate, to a user of the user console 130, that the data point is anomalous and may proceed to provide recommendations, including IOL parameters for optimizing the current patient's surgical outcome. To generate IOL parameters for the current patient, TRG 134 may use another set of trained and deployed ML models 125 that are able to, for example, predict optimal and/or contraindicated IOL parameters for the current patient.

User console 130 also comprises a TDR 131, which receives or generates treatment data regarding the treatment provided to the current patient. As described above, treatment data may include the actual IOL parameters used for the current patient, as well as any additional relevant information, such as the method of performing the cataract surgery etc. As previously defined, actual IOL parameters refer to the type, power, and placement information for the IOL that the surgeon actually implanted in the current patient's eye. In cases where the surgeon does not follow the predicted IOL parameters, the actual IOL parameters would be different from the predicted IOL parameters. In certain such cases, TDR 131 may receive treatment data as user input to a user interface of user console 130. In cases where the surgeon follows the predicted IOL parameters, the actual IOL parameters would be the same as the predicted IOL parameters. In certain such cases, TDR 131 treats the predicted IOL parameters as the actual IOL parameters that are recorded as part of the treatment data. In the embodiments of FIG. 1A, TDR 131 transmits the actual IOL parameters to repository 140 and/or server 120. Repository 140 then augments the current patient's record with the actual IOL parameters used for the treatment.

TRDR 132 generally allows a user of user console 130 to provide post-surgical information identifying surgical outcomes of the treatment. While TRDR 132 is illustrated as executing on user console 130, it should be recognized by one of skill in the art that TRDR 132 can execute on a computing device separate from user console 130. TRDR 132 can allow a user of user console 130 to record patient satisfaction with the ophthalmic surgery procedure (e.g., directly, via ingestion of survey data provided by the patient, etc.), post-surgery data points associated with measurements of anatomical parameters, and other information that may be used to train or re-train ML models 125. TRDR 132 may transmit the treatment result data to repository 140 and/or server 120. Repository 140 augments the current patient's record with the treatment result data.

As described above, model trainer 124 later retrains ML models 125 using the current patient's record, which indicates the current patients' treatment data, treatment result data, data points associated with measurements of anatomical parameters, demographic information, etc.

FIG. 1B illustrates another example computing environment 100B in which training and use of the machine learning models to generate IOL parameters are performed. As illustrated, computing environment 100B includes one or more measurement devices 110, server 120, user console 130, and historical patient data repository 140. In the example of FIG. 1B, TDG 122, model trainer 124, TDR 131, TRDR 132, and TRG 134 all execute on server 120. All of these software modules function identically or at least substantially similar to what was described in relation to FIG. 1A. In the example of FIG. 1B, measurement devices 110 may transmit the data points associated with measurements of anatomical parameters for a current patient to server 120 and/or repository 140. TRG 134 generates the predicted IOL parameters, based in a set of inputs associated with a current patient, and transmits the predicted IOL parameters to user console 130. User console 130 then transmits back treatment data and treatment result data to TDR 131 and TRDR 132, respectively, which process and store the corresponding information at repository 140.

FIG. 1C illustrates an example computing environment 100C in which generating recommendations for parameters of an ophthalmic surgery procedure are performed on a measurement device 110. As illustrated, computing environment 100C includes a measurement device 110, a server 120, and a historical patient data repository 140. In the example of FIG. 1C, TDR 131, TRDR 132, and TRG 134 all execute on a measurement device 110. All of these software modules function identically or at least substantially similar to what was described in relation to FIGS. 1A and 1B.

As illustrated, measurement device 110 includes measurement hardware/software 112, which generally refers to the hardware and software components and modules associated with either an OCT device, a keratometer, or a topography device. Measurement device 110 may also include a user interface and/or a display device, enabling a user to input and/or view information as it relates to the functionality of TDR 131, TRDR 132, and TRG 134.

Figure 2:
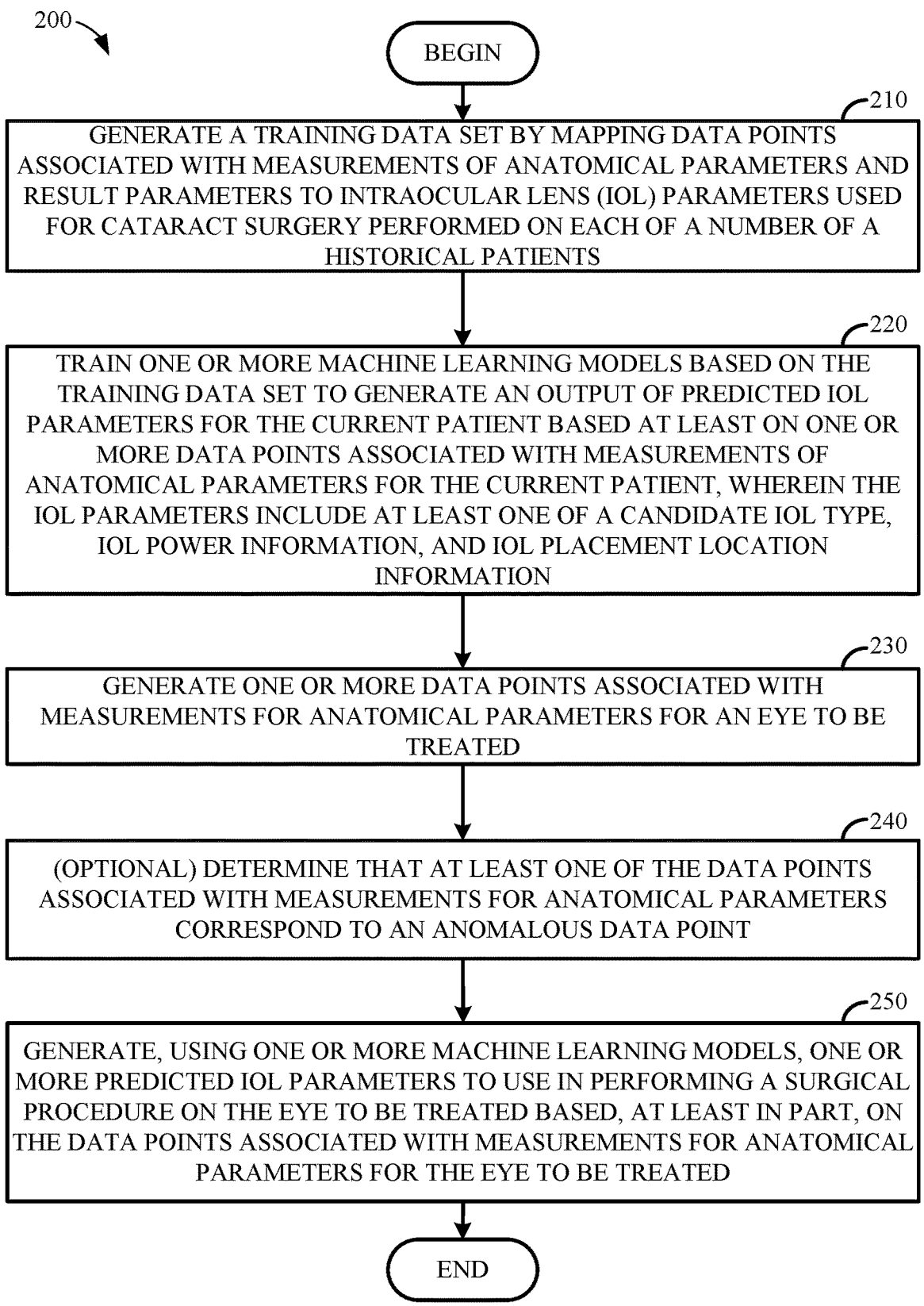
FIG. 2 illustrates example operations that may be performed by computing systems within a networked computing environment to train and use one or more machine learning models to generate recommendations, including IOL parameters, for a patient's cataract surgery based at least on the patient's data points associated with measurements of anatomical parameters, in accordance with certain aspects described herein.

Example Methods for Performing Cataract Surgery Based on Recommendations Generated Using Machine Learning Models FIG. 2 illustrates example operations 200 that may be performed by a computing system to train and use ML models to generate recommendations, including IOL parameters, for a current patient's cataract surgery based at least on data points associated with measurements of anatomical parameters for the current patient, in accordance with certain aspects described herein. Operations 200 may be performed by one or more of a user console 130, server 120, or measurement device 110 illustrated in FIGS. 1A-1C.

As illustrated, operations 200 begin at block 210, where the computing system generates a training data set (or multiple training data sets) used to train one or more machine learning models. The training data set is generally generated by mapping the demographic information and/or data points associated with measurements of anatomical parameters for each historical patient of a number of historical patients to corresponding treatment data (e.g., IOL parameters used for cataract surgery performed on the historical patient, surgical tools, specific surgical methods, etc.) as well as the corresponding treatment result data (e.g., satisfaction or dissatisfaction of the historical patient with the result of the surgery). In some aspects, other information may also be used in the mapping such as surgeon preferences, desired outcomes, and the like.

At block 220, the system trains ML models based on the training dataset(s). The ML models are generally trained to generate recommendations, including predicted optimal and contraindicated IOL parameters for a given patient given an input, including at least the data points associated with measurements of anatomical parameters for the patient. As discussed, the predicted IOL parameters may identify at least one of a candidate IOL type, IOL power information, and IOL placement information for treatment of the current patient. In some aspects, the input to the ML models may include additional information, such as the current patient's demographic information, a desired result of the cataract surgery, whether the patient desires improvement for a specific type of vision (e.g., night vision), surgeon preferences in performing the cataract surgery, and other information that may influence the IOL parameters recommended for the current patient. In certain aspects, the recommendations generated by the ML models may further include recommendations for surgical tools and/or surgical methods to be used as well as additional recommendation that may be helpful to the surgeon in optimizing the surgical outcome.

At block 230, the system generates one or more data points associated with measurements of anatomical parameters for an eye to be treated. The data points generally comprise data generated by an OCT device, a keratometer, a topography device, or other devices that can be used to these data points. The data points may include measurements of the anatomical parameters or data from which such measurements can be derived.

At block 240, the system optionally determines that at least one of the data points associated with measurements of anatomical parameters corresponds to an anomalous data point. As discussed, the system can determine that a data point is anomalous based on a comparison of the data point to a range of values within which typical corresponding data points lie. For example, a data point representing a measurement of an anatomical parameter may typically have a value that is inside a range between a lower bound x and an upper bound y (i.e., nonanomalous data points have values that generally lie between x and y). If the data point has a value less than x or greater than y, the system can determine that the data point is anomalous.

At block 250, the system generates recommendations, including predicted IOL parameters using the one or more trained machine learning models. The recommendations for the IOL to use in performing may be based, at least in part, on the data points associated with measurements of anatomical parameters for the patient as well as the other types of input described with respect to block 220. The generated recommendations may also include additional information, described also with respect to block 220.

Figure 3:
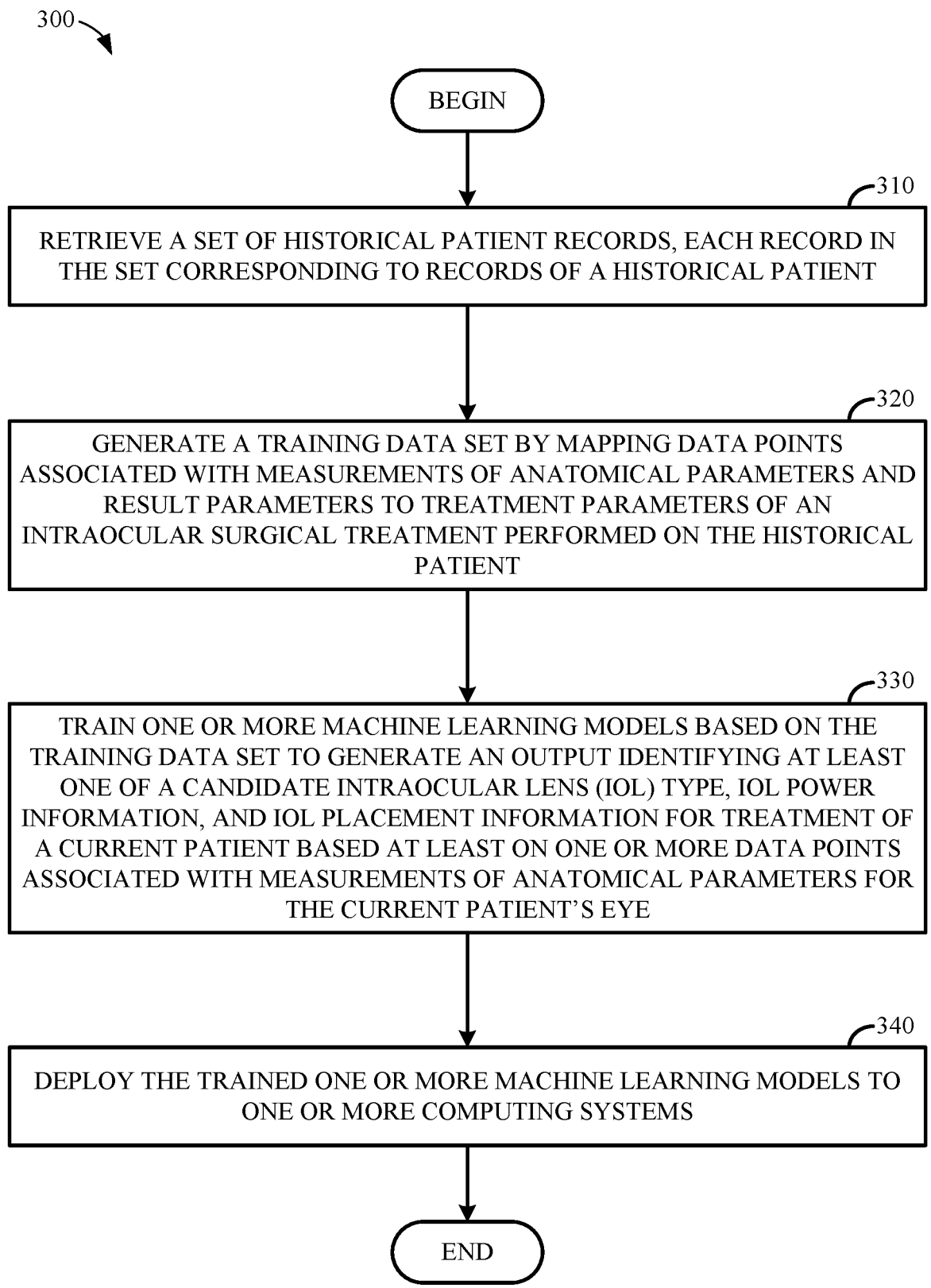
FIG. 3 illustrates example operations that may be performed by one or more computing systems to train one or more machine learning models to generate recommendations, including IOL parameters, for a patient's cataract surgery based on the patient's data points associated with measurements of anatomical parameters, in accordance with certain aspects described herein.

FIG. 3 illustrates example operations 300 that may be performed by a computing system to train one or more machine learning models to generate recommendations, including IOL parameters, for a current patient's cataract surgery based at least on the data points associated with measurements of anatomical parameters for the current patient, in accordance with certain aspects described herein. Operations 300 may be performed, for example, by one or more components of a server in the computing system, such as server 120 illustrated in FIGS. 1A-1C and discussed above (e.g., training data generator 122 and/or model trainer 124).

As illustrated, operations 300 may begin at block 310, where the system retrieves a set of historical patient records. Each record in the set of historical patient records includes information about a specific historical patient. As discussed, for example, each record includes demographic information, data points associated with measurements of anatomical parameters, treatment data, and/or treatment result information recorded for the historical patient.

At block 320, the system generates a training dataset by mapping, for each historical patient of a number of historical patients, the historical patient's demographic information, data points associated with measurements of anatomical parameters for the historical patient, and result parameters to the actual IOL parameters used to treat the historical patient. Generally, by mapping these historical patients' data points and result parameters to their actual IOL parameters, the training dataset may allow for ML models to be trained to predict or otherwise recommend optimal IOL parameters given at least an input of data points associated with measurements of anatomical parameters for a future (i.e., current) patient.

At block 330, the system trains one or more ML models based on the training data set. The trained ML models may be trained to generate one or more recommendations, including optimal IOL parameters for treatment of a current patient given at least the data points associated with measurements of anatomical parameters for the current patient as input. As discussed, the optimal IOL parameters may include at least one of a candidate IOL type, IOL power information, and IOL placement information for treatment of the current patient. In some aspects, the ML models may include a first set of ML models that output optimal IOL parameters and a second set of ML models that output contraindicated or otherwise not recommended IOL parameters. The ML models may be MIMO models or may be a set of MISO models that generate IOL type, IOL power, and IOL placement recommendations individually.

At block 340, the system deploys the trained ML models for use. The trained ML models may be deployed to one or more server computers, a user console, a measurement device in which a computing device is integrated, or the like, as illustrated for example in FIG. 1A-1C, or even a computing device not shown in FIGS. 1A-1C.

Figure 4:
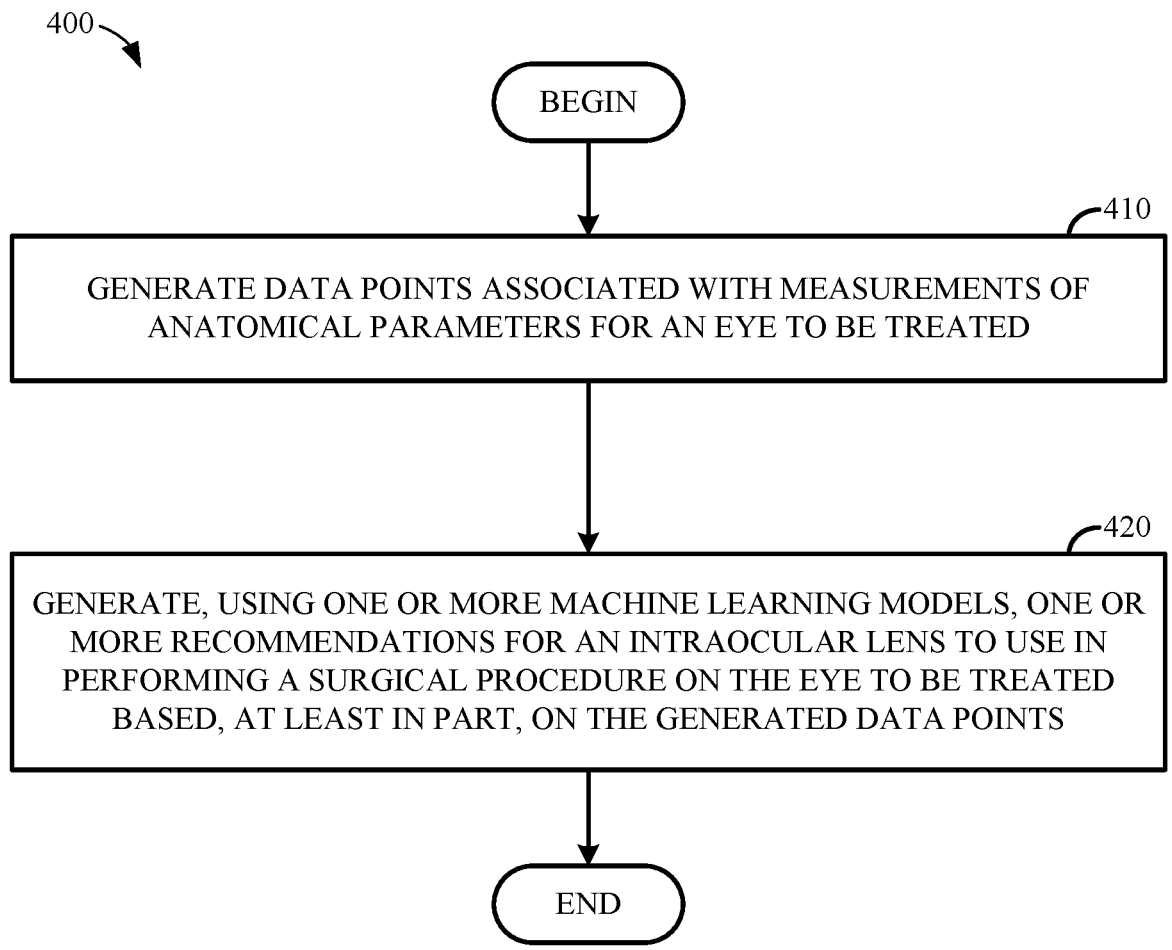
FIG. 4 illustrates example operations that may be performed by one or more computing systems to measure one or more data points associated with measurements of anatomical parameters for an eye to be treated and generate recommendations, including IOL parameters, for a patient's cataract surgery based on the patient's data points, in accordance with certain aspects described herein.

FIG. 4 illustrates example operations 400 that may be performed by a computing system to generate recommendations, including IOL parameters, for a current patient's cataract surgery based at least on data points associated with measurements of anatomical parameters for the current patient, in accordance with certain aspects described herein. Operations 400 may be performed, for example, by a treatment recommendation generator, such as TRG 134 illustrated in FIGS. 1A-1C.

As illustrated, operations 400 may begin at block 410, where the system generates data points associated with measurements of anatomical parameters for an eye to be treated. The data points may include data points obtained by an OCT device, a keratometer, or a topography device. As discussed, the data points may include measurements generated by these devices or raw data from which At block 420, the system generates, using trained ML models, recommendations including optimal IOL parameters. The generated recommendations may be based, at least in part, on the data points provided at block 410. In some aspects, the generated recommendations may be further based on other types of input as described in relation to block 220 of FIG. 2. The recommendations may further include recommendations for surgical tools and/or surgical methods to be used as well as additional recommendation that may be helpful to the surgeon in optimizing the surgical outcome.

Figure 5:
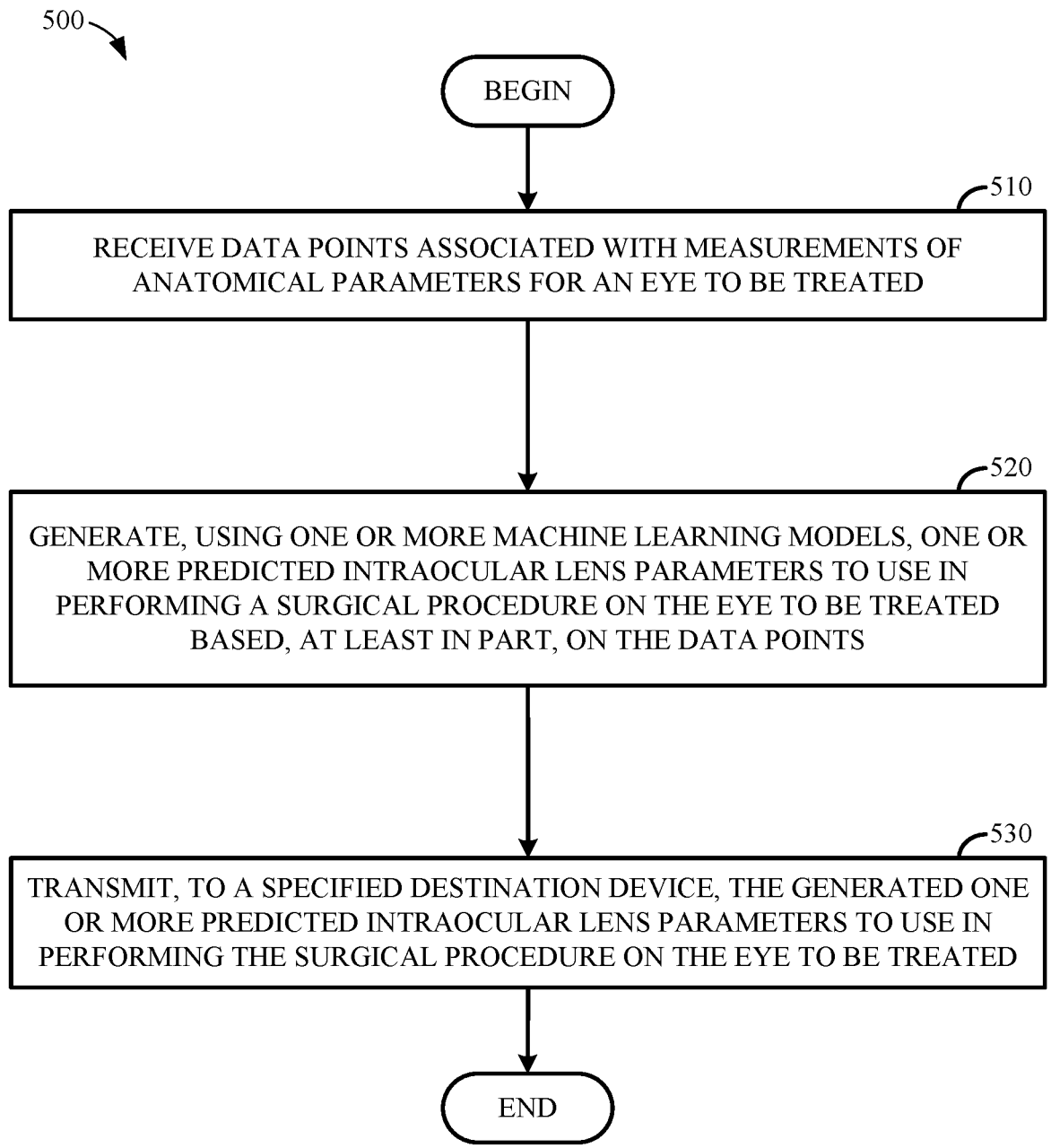
FIG. 5 illustrates example operations that may be performed by one or more computing systems to generate and output recommendations, including IOL parameters, for a patient's cataract surgery based on the patient's data points associated with measurements of anatomical parameters, in accordance with certain aspects described herein.

FIG. 5 illustrates example operations 500 that may be performed by one or more computing systems to generate recommendations, including IOL parameters, for a current patient's cataract surgery based at least on data points associated with measurements of anatomical parameters for the current patient, in accordance with certain aspects described herein. Operations 500 may be performed, for example, by a treatment recommendation generator, such as TRG 134 illustrated in FIGS. 1A-1C.

At block 510, the system receives data points associated with measurements of anatomical parameters for an eye to be treated.

At block 520, the system generates, using trained ML models, one or more recommendations including IOL parameters for a cataract surgery to be performed on the current patient. The generated recommendations may be based, at least in part, on the data points.

At block 530, the system transmits, to a specified destination device, the generated one or more recommendations. The specified destination device may be a user console through which planning for ophthalmic surgery is performed (which may be communicatively coupled with one or more measurement devices via a network or a point-to-point connection or integral with a measurement device) or a device capable of receiving electronic messaging from another device.

Figure 6:
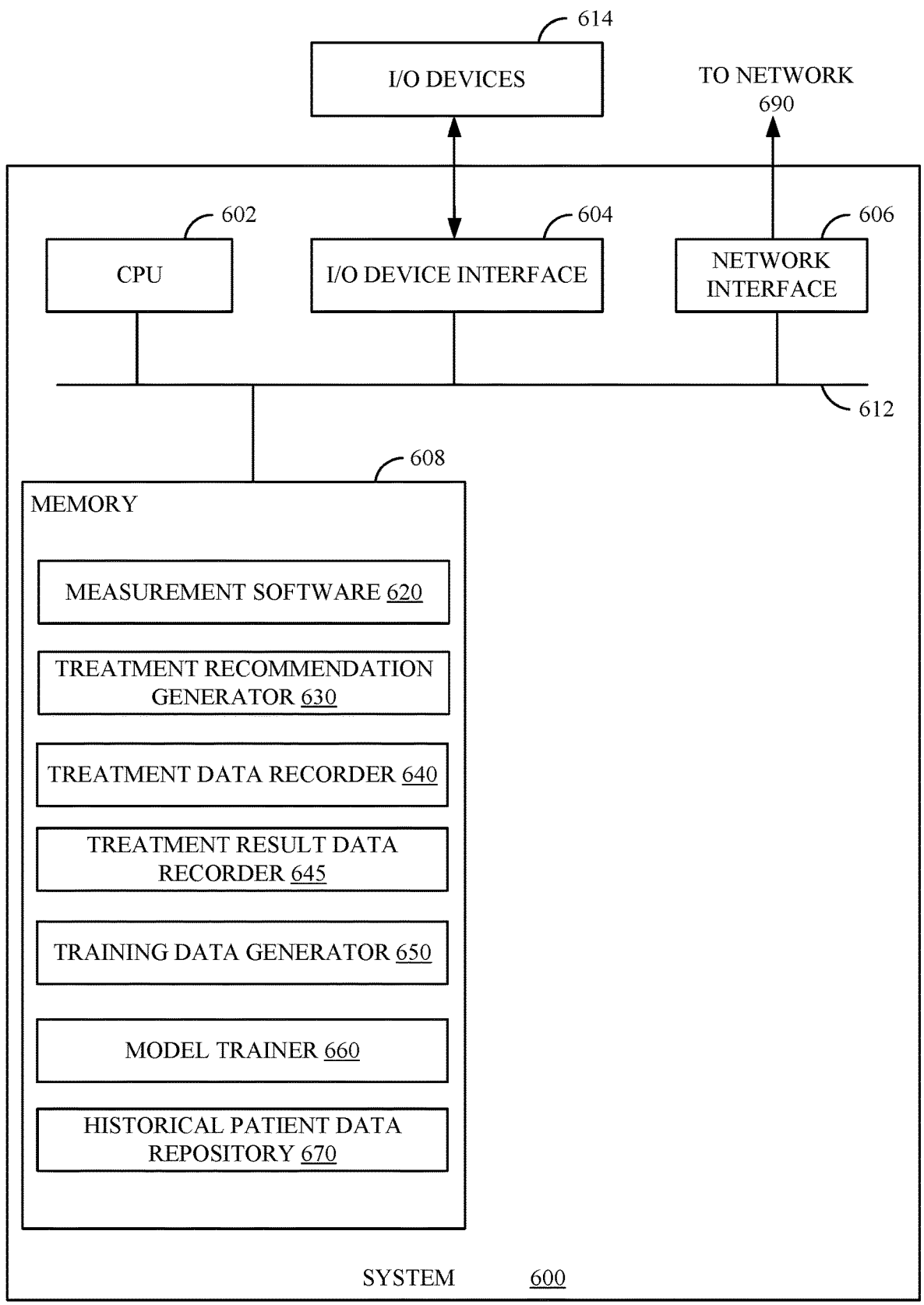
FIG. 6 illustrates an example system on which embodiments of the present disclosure can be performed.

Example System for Performing Cataract Surgery Based on Recommendations Generated Using Machine Learning Models FIG. 6 illustrates an example system 600 that uses machine learning models to aid in performing surgical ophthalmic procedures, such as cataract surgeries. For example, system 600 may comprise one or more of the measurement devices 110, server 120, and/or user console 130 illustrated in FIG. 1.

As shown, system 600 includes a central processing unit (CPU) 602, one or more I/O device interfaces 604 that may allow for the connection of various I/O devices 614 (e.g., keyboards, displays, mouse devices, pen input, etc.) to the system 600, network interface 606 through which system 600 is connected to network 690 (which may be a local network, an intranet, the internet, or any other group of computing devices communicatively connected to each other), a memory 608, storage 610, and an interconnect 612.

CPU 602 may retrieve and execute programming instructions stored in the memory 608. Similarly, the CPU 602 may retrieve and store application data residing in the memory 608. The interconnect 612 transmits programming instructions and application data, among the CPU 602, I/O device interface 604, network interface 606, memory 608, and storage 610.

CPU 602 is included to be representative of a single CPU, multiple CPUs, a single CPU having multiple processing cores, and the like.

Memory 608 is representative of a volatile memory, such as a random access memory, and/or a nonvolatile memory, such as nonvolatile random access memory, phase change random access memory, or the like. As shown, memory 608 includes measurement software or instructions 620, TRG 630, TDR 640, TRDR 645, TDG 650, model trainer 660, and repository 670. Measurement software 620 is generally configured to receive raw image or reflectivity data from optical hardware that is a part of system 600 (e.g., OCT scanner, etc.) or a connected measurement device (e.g., OCT device, keratometer, topography device) and generate data points associated with measurements of one or more anatomical parameters therefrom. Measurement software 620 may output the data points associated with measurements of anatomical parameters to TRG 630 for use in providing recommendations, including predicting optimal IOL parameters for a surgical ophthalmic procedure.

TRG 630 comprises or uses one or more trained and deployed ML models trained by model trainer 660. TRG 630 generally processes at least one or more data point associated with a measurement of an anatomical parameter received from measurement software 620 or from an external source and generates, using the one or more ML models, one or more recommendations including optimal and/or contraindicated IOL parameters for the patient's eye.

TDR 640 generally allows for a user of system 600 to record actual treatment data, as previously defined. TDR 640 may aggregate the actual IOL parameters used for a patient and output the data to repository 670 for storage and future use in generating training datasets used to train the one or more ML models deployed to and used by TRG 630. TRDR 645 generally allows for a user of system 600 to record information, such as results parameters, about the outcome of an ophthalmic surgical procedure. TRDR 645 may aggregate the recorded outcome information and output the data to historical patient data repository 670 for storage and future use in generating training data sets used to train the one or more machine learning models deployed to and used by TRG 630.

As discussed, TDG 650 generally uses historical patient information (e.g., stored in historical patient data repository 670) to generate training data sets that may be used by model trainer 660 to train the one or more ML models deployed to and used by treatment recommendation generator 630.

Model trainer 660 generally trains the one or more ML models used by treatment recommendation generator 630 in predicting optimal (and, in some aspects, contraindicated) IOL parameters for an ophthalmic surgical procedure. As discussed, model trainer 660 may use the training data sets generated by training data generator 650 to train the ML models and may deploy the trained ML models to TRG 630 (or a remote system) for use.

Additional Considerations

The preceding description is provided to enable any person skilled in the art to practice the various embodiments described herein. Various modifications to these embodiments will be readily apparent to those skilled in the art, and the generic principles defined herein may be applied to other embodiments. For example, changes may be made in the function and arrangement of elements discussed without departing from the scope of the disclosure. Various examples may omit, substitute, or add various procedures or components as appropriate. Also, features described with respect to some examples may be combined in some other examples. For example, an apparatus may be implemented or a method may be practiced using any number of the aspects set forth herein. In addition, the scope of the disclosure is intended to cover such an apparatus or method that is practiced using other structure, functionality, or structure and functionality in addition to, or other than, the various aspects of the disclosure set forth herein. It should be understood that any aspect of the disclosure disclosed herein may be embodied by one or more elements of a claim.

As used herein, a phrase referring to "at least one of" a list of items refers to any combination of those items, including single members. As an example, "at least one of: a, b, or c" is intended to cover a, b, c, a-b, a-c, b-c, and a-b-c, as well as any combination with multiples of the same element (e.g., a-a, a-a-a, a-a-b, a-a-c, a-b-b, a-c-c, b-b, b-b-b, b-b-c, c-c, and c-c-c or any other ordering of a, b, and c).

As used herein, the term "determining" encompasses a wide variety of actions. For example, "determining" may include calculating, computing, processing, deriving, investigating, looking up (e.g., looking up in a table, a database or another data structure), ascertaining and the like. Also, "determining" may include receiving (e.g., receiving information), accessing (e.g., accessing data in a memory) and the like. Also, "determining" may include resolving, selecting, choosing, establishing and the like.

The methods disclosed herein comprise one or more steps or actions for achieving the methods. The method steps and/or actions may be interchanged with one another without departing from the scope of the claims. In other words, unless a specific order of steps or actions is specified, the order and/or use of specific steps and/or actions may be modified without departing from the scope of the claims. Further, the various operations of methods described above may be performed by any suitable means capable of performing the corresponding functions. The means may include various hardware and/or software component(s) and/or module(s), including, but not limited to a circuit, an application specific integrated circuit (ASIC), or processor. Generally, where there are operations illustrated in figures, those operations may have corresponding counterpart means-plus-function components with similar numbering.

The various illustrative logical blocks, modules and circuits described in connection with the present disclosure may be implemented or performed with a general purpose processor, a digital signal processor (DSP), an application specific integrated circuit (ASIC), a field programmable gate array (FPGA) or other programmable logic device (PLD), discrete gate or transistor logic, discrete hardware components, or any combination thereof designed to perform the functions described herein. A general-purpose processor may be a microprocessor, but in the alternative, the processor may be any commercially available processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

A processing system may be implemented with a bus architecture. The bus may include any number of interconnecting buses and bridges depending on the specific application of the processing system and the overall design constraints. The bus may link together various circuits including a processor, machine-readable media, and input/output devices, among others. A user interface (e.g., keypad, display, mouse, joystick, etc.) may also be connected to the bus. The bus may also link various other circuits such as timing sources, peripherals, voltage regulators, power management circuits, and the like, which are well known in the art, and therefore, will not be described any further. The processor may be implemented with one or more general-purpose and/or special-purpose processors. Examples include microprocessors, microcontrollers, DSP processors, and other circuitry that can execute software. Those skilled in the art will recognize how best to implement the described functionality for the processing system depending on the particular application and the overall design constraints imposed on the overall system.

If implemented in software, the functions may be stored or transmitted over as one or more instructions or code on a computer-readable medium. Software shall be construed broadly to mean instructions, data, or any combination thereof, whether referred to as software, firmware, middleware, microcode, hardware description language, or otherwise. Computer-readable media include both computer storage media and communication media, such as any medium that facilitates transfer of a computer program from one place to another. The processor may be responsible for managing the bus and general processing, including the execution of software modules stored on the computer-readable storage media. A computer-readable storage medium may be coupled to a processor such that the processor can read information from, and write information to, the storage medium. In the alternative, the storage medium may be integral to the processor. By way of example, the computer-readable media may include a transmission line, a carrier wave modulated by data, and/or a computer readable storage medium with instructions stored thereon separate from the wireless node, all of which may be accessed by the processor through the bus interface. Alternatively, or in addition, the computer-readable media, or any portion thereof, may be integrated into the processor, such as the case may be with cache and/or general register files. Examples of machine-readable storage media may include, by way of example, RAM (Random Access Memory), flash memory, ROM (Read Only Memory), PROM (Programmable Read-Only Memory), EPROM (Erasable Programmable Read-Only Memory), EEPROM (Electrically Erasable Programmable Read-Only Memory), registers, magnetic disks, optical disks, hard drives, or any other suitable storage medium, or any combination thereof. The machine-readable media may be embodied in a computer-program product.

A software module may comprise a single instruction, or many instructions, and may be distributed over several different code segments, among different programs, and across multiple storage media. The computer-readable media may comprise a number of software modules. The software modules include instructions that, when executed by an apparatus such as a processor, cause the processing system to perform various functions. The software modules may include a transmission module and a receiving module. Each software module may reside in a single storage device or be distributed across multiple storage devices. By way of example, a software module may be loaded into RAM from a hard drive when a triggering event occurs. During execution of the software module, the processor may load some of the instructions into cache to increase access speed. One or more cache lines may then be loaded into a general register file for execution by the processor. When referring to the functionality of a software module, it will be understood that such functionality is implemented by the processor when executing instructions from that software module.

The following claims are not intended to be limited to the embodiments shown herein, but are to be accorded the full scope consistent with the language of the claims. Within a claim, reference to an element in the singular is not intended to mean "one and only one" unless specifically so stated, but rather "one or more." Unless specifically stated otherwise, the term "some" refers to one or more. No claim element is to be construed under the provisions of 35 U.S.C. § 112(f) unless the element is expressly recited using the phrase "means for" or, in the case of a method claim, the element is recited using the phrase "step for." All structural and functional equivalents to the elements of the various aspects described throughout this disclosure that are known or later come to be known to those of ordinary skill in the art are expressly incorporated herein by reference and are intended to be encompassed by the claims. Moreover, nothing disclosed herein is intended to be dedicated to the public regardless of whether such disclosure is explicitly recited in the claims.

What is claimed is:

1. A method of determining one or more intraocular lens (IOL) parameters for an IOL to be used in a cataract surgery procedure, comprising:
   generating, using one or more measurement devices, one or more data points associated with measurements of anatomical parameters for an eye to be treated; and
   generating, using one or more trained machine learning models, one or more recommendations including one or more IOL parameters for the IOL to be used in the cataract surgery based, at least in part, on the one or more data points associated with measurements of anatomical parameters for the eye to be treated, wherein:
      the one or more trained machine learning models are trained based on at least one historical data set, wherein each entry in the historical dataset includes one more data points associated with measurements of anatomical parameters for a historical patient mapped to treatment data and treatment result data associated with the historical patient, wherein:
      the treatment data associated with the historical patient indicates at least one or more actual IOL parameters of a corresponding IOL used for treating the historical patient;
      the treatment result data associated with the historical patient indicates at least one or more result parameters indicative of the historical patient's surgical outcome, and the one or more IOL parameters comprise one or more of a type of IOL to use, a power of the IOL, or placement information for implanting the IOL in the eye.

2. The method of claim 1, wherein the one or more data points comprise measurements derived from one or more of a cross-sectional view of the eye, a topographic map of the eye, or a light pattern reflection associated with the eye.

3. The method of claim 1, wherein the one or more data points comprise raw data generated by the one or more measurement devices from which measurements of anatomical parameters can be derived.

4. The method of claim 1, further comprising:
   determining, based on a comparison of the one or more data points to a distribution of data points representing nonanomalous measurements of historical patients, that at least one of the one or more data points corresponds to an anomalous measurement, wherein the one or more recommendations are generated further based on the determination that at least one of the one or more data points corresponds to an anomalous measurement.

5. The method of claim 1, wherein generating the one or more recommendations including one or more IOL parameters for the IOL to be used in the cataract surgery is further based on a targeted result of the treatment.

6. The method of claim 1, wherein the one or more trained machine learning models comprise a multi-output machine learning model that generates, for the one or more data points associated with measurements of anatomical parameters, an output identifying a candidate lens type, lens power, and lens placement location.

7. The method of claim 1, wherein the one or more trained machine learning models comprise a first set of machine learning models configured to identify recommended IOL parameters and a second set of machine learning models configured to identify contraindicated IOL parameters for the eye to be treated.

8. The method of claim 7, wherein the first set of machine learning models is configured to identify recommended IOL parameters based on a satisfaction metric indicating patient satisfaction with each treatment in a training data set used to train the first set of machine learning models, and the second set of machine learning models is configured to identify contraindicated IOL parameters based on a satisfaction metric indicating patient dissatisfaction with each treatment in a training data set used to train the second set of machine learning models.

9. The method of claim 1, wherein the one or more recommendations is further generated based on one or more additional data points indicating a user preference in applying a treatment to the eye to be treated.

10. The method of claim 1, further comprising:
   recording an outcome of the treatment; and
   adding a mapping of the type of IOL and placement for the intraocular lens to the recorded outcome of the treatment to a training data set for use in re-training the one or more machine learning models.

11. The method of claim 1, further comprising:
identifying, using the one or more trained machine learning models, previous treatments associated with similar data points associated with measurements of anatomical parameters;
retrieving additional information associated with the identified previous treatments; and
outputting the additional information for display.

12. The method of claim 1, wherein generating the one or more data points associated with measurements of anatomical parameters for the eye to be treated comprises:
generating a cross-sectional view of the eye, and
measuring one or more anatomical parameters based on the generated cross-sectional view, wherein the one or more anatomical measurements comprise one or more of an axial length measurement, corneal thickness measurement, chamber depth measurement, or lens thickness measurement.

13. The method of claim 1, wherein generating the one or more data points associated with measurements of anatomical parameters for the eye to be treated comprises generating, based on a light pattern analysis, a topographic map of the eye, the topographic map showing at least a measured curvature of the eye.

14. A method for performing a cataract surgery procedure, comprising:
generating a training data set from a set of historical patient records, wherein each record in the training data set corresponds to a historical patient and comprises information identifying:
data points associated with measurements of one or more anatomical parameters for the historical patient,
one or more intraocular lens (IOL) parameters of a corresponding IOL used in a cataract surgery procedure performed on the historical patient, and
treatment result data identifying an outcome of the intraocular treatment performed on the historical patient;
training one or more machine learning models based on the training data set to generate an output identifying at least one of a candidate IOL type, IOL power information, and IOL placement information for treatment of a current patient based at least on data points associated with measurements of one or more anatomical parameters for the current patient's eye;
generating, using one or more measurement instruments, data points associated with measurements of one or more anatomical parameters for the current patient's eye;
determining, based on a comparison of the one or more generated data points to a distribution of data points representing nonanomalous data points for historical patients, that at least one of the one or more data points corresponds to an anomalous data point; and
based on determining that at least one of the one or more data points corresponds to an anomalous data point, generating, using the one or more trained machine learning models, one or more recommended IOL parameters for the current patient's eye based, at least in part, on the data points, wherein the one or more recommended IOL parameters comprise one or more of an IOL type, an IOL power, or IOL placement information for implanting the IOL in the eye.

15. The method of claim 14, wherein the measurements of the one or more anatomical parameters comprise one or more of an axial length measurement, a corneal thickness measurement, a chamber depth measurement, a lens thickness measurement, and a measured curvature of the eye being treated.

16. The method of claim 14, wherein training the one or more machine learning models comprises training a first set of machine learning models configured to identify recommended IOL parameters for the current patient's eye and training a second set of machine learning models configured to identify contraindicated IOL parameters for the current patient's eye.

17. The method of claim 14, wherein generating the one or more recommended IOL parameters is further based on a targeted result of the treatment.

18. The method of claim 14, wherein the one or more trained machine learning models comprise a multi-output machine learning model that generates, for one or more data points associated with measurements of anatomical parameters for the current patient's eye, an output identifying a candidate lens type, lens power, and lens placement location.

19. The method of claim 14, wherein the one or more trained machine learning models comprise a first set of machine learning models configured to identify recommended IOL parameters for the current patient's eye and a second set of machine learning models configured to identify contraindicated IOL parameters for the current patient's eye.

20. The method of claim 19, wherein the first set of machine learning models is configured to identify recommended IOL parameters for the current patient's eye based on a satisfaction metric indicating patient satisfaction with each treatment in a training data set used to train the first set of machine learning models, and the second set of machine learning models is configured to identify contraindicated IOL parameters for the current patient's eye based on a satisfaction metric indicating patient dissatisfaction with each treatment in a training data set used to train the second set of machine learning models.

21. The method of claim 14, wherein the one or more recommended IOL parameters is generated further based on one or more additional data points indicating a user preference in applying a treatment to the current patient's eye.

22. The method of claim 14, further comprising:
recording an outcome of the treatment; and
adding a mapping of the IOL type, IOL power, and IOL placement information for the current patient to the recorded outcome of the treatment to a training data set for use in re-training the one or more machine learning models.

23. The method of claim 14, further comprising:
identifying, using the one or more trained machine learning models, previous treatments having similar data points associated with measurements of anatomical parameters;
retrieving additional information associated with the identified previous treatments; and
outputting the additional information for display.

24. The method of claim 14, wherein generating the data points associated with measurements of anatomical parameters for the current patient's eye comprises:
generating a cross-sectional view of the current patient's eye, and
measuring one or more optical parameters based on the generated cross-sectional view, wherein the one or more optical parameters comprise one or more of an axial length measurement, corneal thickness measurement, chamber depth measurement, or lens thickness measurement.

25. The method of claim 14, wherein generating the data points associated with measurements of anatomical parameters for the current patient's eye comprises generating, based on a light pattern analysis, a topographic map of the eye being treated, the topographic map showing at least a measured curvature of the eye being treated.

* * * * *